United States Patent [19]

Seitz et al.

[11] Patent Number: 5,453,531
[45] Date of Patent: Sep. 26, 1995

[54] SUBSTITUTED VALINAMIDE DERIVATIVES

[75] Inventors: Thomas Seitz, Monheim; Detlef Wollweber, Wuppertal; Wilhelm Brandes, Leichlingen; Heinz-Wilhelm Dehne, Monheim, all of Germany

[73] Assignee: Bayer Aktiengesellschaft, Leverkusen, Germany

[21] Appl. No.: 134,015

[22] Filed: Oct. 7, 1993

Related U.S. Application Data

[63] Continuation-in-part of Ser. No. 819,047, Jan. 10, 1992, abandoned, which is a continuation-in-part of Ser. No. 747,056, Aug. 19, 1991, abandoned.

[30] Foreign Application Priority Data

Aug. 25, 1990 [DE] Germany ............................ 40 26 966.3

[51] Int. Cl.⁶ .......................... G07C 271/16; A01N 47/12
[52] U.S. Cl. .................... 560/29; 560/24; 560/30
[58] Field of Search ................ 560/24, 29, 30; 514/487

[56] References Cited

U.S. PATENT DOCUMENTS 5,210,084   5/1993   Wollweber et al. ............... 514/237.5

FOREIGN PATENT DOCUMENTS 0398072   5/1990   European Pat. Off. .

OTHER PUBLICATIONS

Chemical Abstracts, vol. 110, Apr. 10, 1989, No. 15.

Primary Examiner—Josë G. Dees
Assistant Examiner—Barbara S. Frazier
Attorney, Agent, or Firm—Sprung Horn Kramer & Woods

[57] ABSTRACT

Fungicidal substituted valinamide derivatives of the formula

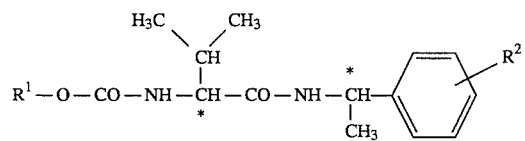

in which
$R^1$ represents i-propyl or s-butyl, and
$R^2$ represents chlorine, methyl, ethyl or methoxy.

29 Claims, No Drawings

SUBSTITUTED VALINAMIDE DERIVATIVES

This is a continuation-in-part of application Ser. No. 07/819,047, filed Jan. 10, 1992, now abandoned, which is a continuation-in-part of application Ser. No. 07/747,056, filed Aug. 19, 1991, now abandoned.

The invention relates to new valinamide derivatives, to a process for their preparation, and to their use as pesticides, in particular as fungicides.

The substances according to the invention have an outstanding action in the control of pests. In particular, they can be used as fungicides, mainly in plant protection.

Certain amino acid amides have already been disclosed (cf., for example, EP-A 236,874). However, the use of these compounds in pesticides has not been described.

New valinamide derivatives of the general formula (I)

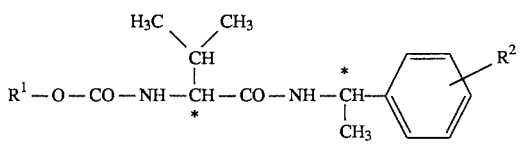

in which
R$^1$ represents i-propyl or s-butyl and
R$^2$ represents chlorine, methyl, ethyl or methoxy, in the 3- or 4- position
have now been found.

The compounds of the formula (I) contain two centres of chirality and can therefore exist in various mixtures of enantiomers and diastereomers, which, if appropriate, can be resolved in the customary fashion. The invention claims the pure enantiomers and diastereomers as well as the mixtures.

For simplicity's sake, the following text will always mention compounds of the formula (I), even though this is understood as meaning the pure compounds as well as the mixtures having various proportions of isomeric, enantiomeric and diastereomeric compounds.

The valinamide derivatives of the general formula (I)

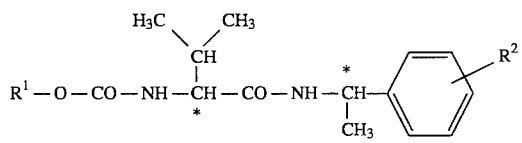

in which
R$^1$ represents i-propyl or s-butyl and
R$^2$ represents chlorine, methyl, ethyl or methoxy in the 3- or 4- position
are obtained when a substituted amino acid of the formula (II)

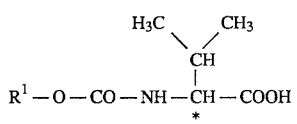

in which
R$^1$ represents i-propyl or s-butyl, or their carboxyl-activated derivatives,
is reacted with an amine of the formula (III)

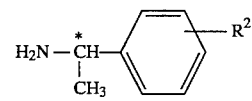

in which
R$^2$ represents chlorine, methyl, ethyl or methoxy, in the 3- or 4- position
if appropriate in the presence of a catalyst, if appropriate in the presence of an acid-binding agent and if appropriate in the presence of a diluent.

If, for example, i-propyloxycarbonyl-L-valine and 4-chlorophenethylamine are used as starting materials, the course of the process according to the invention can be illustrated by the following equation:

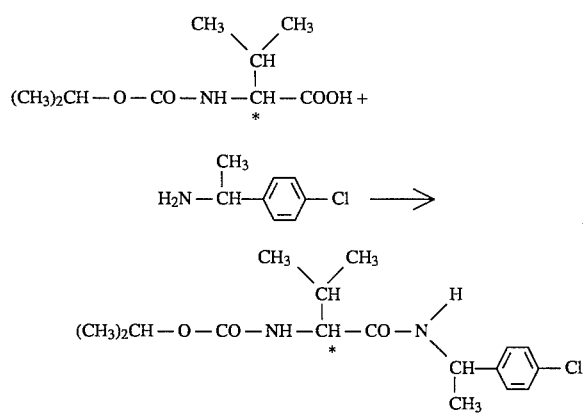

Preferred compounds of the formula (I) are those in which the basic amino acid of the formula (II) is i-propyloxycarbonyl-L-valine or s-butoxycarbonyl-L-valine and the phenethylamine of the formula (III) employed, in which
R$^2$ represents chlorine, methyl, ethyl or methoxy,
is either racemic or has the R(+) configuration or the S(−) configuration on the asymmetric centre.

Particularly preferred compounds of the formula (I) are those in which the basic amino acid is i-propyloxy-carbonyl-L-valine or s-butoxycarbonyl-L-valine and the phenethylamine employed, in which
R$^2$ represents chlorine, methyl, ethyl or methoxy,
is either racemic or has the R(+) configuration on the asymmetric centre.

Formula (II) provides a general definition of the amino acid derivatives to be used as starting substances for carrying out the process according to the invention. In this formula, R$^1$ and R$^2$ preferably have the meanings which have already been mentioned in connection with the description of the substances of the formula (I) according to the invention as being preferred for these substituents.

The amino acid derivatives of the formula (II) are generally known (cf., for example, Houben-Weyl, Methoden der organischen Chemie [Methods in Organic Chemistry], Volume XV, parts 1 and 2, pages 46 et seq. and 112 et seq., Georg Thieme Verlag, Stuttgart 1974; D. Keller et. al., Org. Synth. 60, 2145 (1981); or R. C. Sheppard, A Specialist Periodical Report, Amino-acids, Peptides and Proteins, The Royal Society of Chemistry, Burlington House, London 1978, or I. P. Greenstein and M. Winitz, Chemistry of Amino Acids, I. Wiley Sons Inc., New York, London 1961; or E. Schröder and K. Lübke, The Peptides Vol. I, Academic Press, New York, London 1965) or they can be obtained by the processes described in these publications.

The carboxyl-activated derivatives of the amino acid of the formula (II) which are furthermore to be used as starting substances for carrying out the process according to the invention are generally known.

Suitable carboxyl-activated derivatives of the amino acids of the formula (II) are all carboxyl-activated derivatives, such as acid halides such as, for example, acid chlorides, acid azides, furthermore symmetric and mixed anhydrides such as, for example, the mixed O-alkylcarbonic anhydrides, furthermore activated esters such as, for example, p-nitrophenyl esters or N-hydroxysuccinimide esters, or activated forms of the amino acids which have been prepared in situ using condensing agents such as, for example, dicyclohexylcarbodiimide or carbonyldiimidazol.

It is preferred to employ the acid chlorides and mixed anhydrides which correspond to the amino acids of the formula (II). They can be prepared by reacting the amino acids of the formula (II) or their salts with a halogenating agent or with one of the generally known agents for the preparation of mixed anhydrides, such as, for example, phosphorus pentachloride, thionyl chloride, oxalyl chloride or isobutyl chloroformate, in a generally known fashion. The use of isobutyl chloroformate is preferred.

The reaction can be carried out in the presence of inert diluents such as, for example, aromatic, non-aromatic or halogenated hydrocarbons such as: ketones such as, for example, acetone; esters such as, for example, ethyl acetate; amides such as, for example, dimethylformamide, nitriles such as, for example, acetonitrile, chlorohydrocarbons such as, for example, methylene chloride, hydrocarbons such as, for example, toluene; or ethers such as, for example, tetrahydrofuran, or their mixtures, and/or in the presence of an acid-binding agent such as, preferably, a tertiary amine such as, for example, triethylamine, pyridine or N-methylpiperidine, at temperatures from −78° C. to 100° C., preferably from −60° C. to 25° C.

Formula (III) provides a general definition of the amines furthermore to be used as starting substances for carrying out the process according to the invention. In these formulae, $R^2$ has the abovementioned meanings The amines of the formula (III) are generally known compounds of organic chemistry.

Diluents which are suitable for the process according to the invention are inert, organic solvents such as: ketones such as acetone or ethyl methyl ketone; esters such as ethyl acetate or methyl acetate; amides such as dimethylformamide; nitriles such as acetonitrile; chlorohydrocarbons such as methylene chloride or carbon tetrachloride; hydrocarbons such as toluene, or ethers such as tetrahydrofuran, and, if appropriate, water, and mixtures of the above.

Acid-binding agents which are suitable for the process according to the invention are customary inorganic and organic acid binders. These preferably include tertiary amines such as triethylamine, pyridine or N-methylpiperidine, and also inorganic bases, such as metal hydroxides such as sodium hydroxide and potassium hydroxide, or metal carbonates such as sodium carbonate or calcium carbonate.

If appropriate, the process according to the invention is carried out in the presence of a catalyst. The following may be mentioned by way of example: 4-dimethylaminopyridine, 1-hydroxy-benzotriazole or dimethylformamide.

When carrying out the process, the temperatures can be varied within a substantial range. In general, the process is carried out between −78 to +120° C., preferably at −60° to +40 ° C.

It is preferred to carry out the process according to the invention in equimolar amounts.

In this context, the amino acid derivatives of the formula (II) are employed as pure optical isomers (D or L form) or as racemates.

The invention embraces the pure isomers as well as the mixtures. These mixtures can be resolved into the components by customary methods, for example selective crystallisation from suitable solvents or chromatography on silica gel or on aluminium oxide. Racemates can be resolved to give the individual enantiomers using customary methods, for example by salt formation with optically active acids such as camphorsulphonic acid or dibenzoyltartaric acid and selective crystallisation, or by the formation of the derivatives with suitable, optically active reagents, separation of the diastereomeric derivatives and cleavage or separation on optically active column material.

The active compounds of the formula (I) according to the invention have a powerful action against pests and can be employed in practice for combating undesired harmful organisms. The active compounds are suitable for use as plant protection agents, in particular as fungicides.

Fungicides in plant protection are employed for combating plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*;
Phytophthora species, such as, for example, *Phytophthora infestans*;
Pseudoperonospora species, such as, for example, *Pseudoperonospora humuli* or *Pseudoperonospora cubensis*;
Plasmopara species, such as, for example, *Plasmopara viticola*;
Peronospora species, such as, for example, *Peronospora pisi* or *P. brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus*;
Puccinia species, such as, for example, *Puccinia recondita*;
Tilletia species, such as, for example, *Tilletia caries*;
Ustilago species, such as, for example, *Ustilago nuda* or *Ustilago avenae*;
Pellicularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Septoria species, such as, for example, *Septoria nodorum*;
Leptosphaeria species, such as, for example, *Leptosphaeria nodorum*;
Cercospora species, such as, for example, *Cercospora canescens*;

Alternaria species, such as, for example, *Alternaria brassicae* and

Pseudocercosporella species, such as, for example, *Pseudocercosporella herpotrichoides*.

The good toleration, by plants, of the active compounds, in the concentrations required for combating plant diseases, permits treatment of above-ground parts of plants, of vegetative propagation stock and seeds, and of the soil.

The active compounds according to the invention are particularly suitable for protectively combating Phytophthora species on tomatoes or Plasmopara species on vines.

Moreover, the active compounds also show a leaf-acting insecticidal action.

Depending on their particular physical and/or chemical properties, the active compounds can be converted into customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl, polyglycol ethers, alkylsulphonates, alkyl sulphates, arylsulphonates as well as albumen hydrolysis products; as dispersing agents there are suitable: for example lignin sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilisers and growth regulators.

The active compounds can be used as such, in the form of their formulations or of the use forms prepared therefrom, such as ready-for-use solutions, suspensions, wettable powders, pastes, soluble powders, dusts and granules. They are applied in the customary manner, for example by pouring, spraying, atomising, scattering, dusting, foaming, brushing on and the like. It is furthermore possible to apply the active compounds by the ultra-low volume method or to inject the preparation of active compound, or the active compound itself, into the soil. The seed of plants can also be treated.

In the treatment of parts of plants, the active compound concentrations in the use forms can be varied within a substantial range. They are generally between 1 and 0.0001% by weight, preferably between 0.5 and 0.001%.

In the treatment of seed, amounts of active compound of 0.001 to 50 g, preferably 0.01 to 10 g, are generally required per kilogram of seed.

In the treatment of the soil, active compound concentrations of 0.00001 to 0.1% by weight, preferably 0.0001 to 0.02%, are required at the site of action.

In the treatment of animal pests, the active compound concentrations are generally between 0.0000001 up to 95% of active compound, preferably between 0.0001 to 1%.

PREPARATION EXAMPLES

Example 1

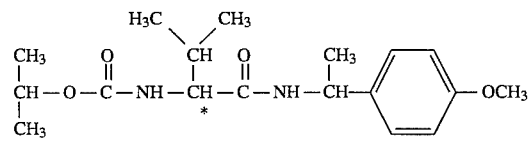

2.3 g (0.023 mol) of N-methylpiperidine were added at −20° C. to 4.67 g of i-propoxycarbonyl-L-valine (0.023 mol), dissolved in 50 ml of $CH_2Cl_2$. 3.2 g (0.023 mol) of isobutyl chloroformate are then rapidly added dropwise at −20° C., stirring is continued at the same temperature for 10 minutes, and the mixture is then cooled to −60° C., and 3.5 g (0.023 mol) of 4-methoxy-1-phenylethylamine are run in, during which process the temperature is kept below −15° C. After 2 hours at −15° C., stirring is continued for 15 hours at room temperature, solids are filtered off and rinsed with $CH_2Cl_2$, the filtrate is concentrated, the residue is introduced into water, the mixture is extracted twice using ethyl acetate, and the combined ethyl acetate phases are washed with $NaHCO_3$ solution and water, dried and concentrated. 4.64 g (60% of theory) of N-(i-propyl-oxycarbonyl)-L-valine-4-methoxyphenylethylamide of melting point 167° C. are obtained.

The following compounds of the formula (I) are obtained analogously to Example 1

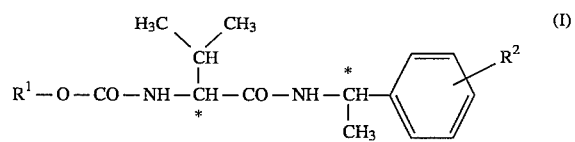

(I)

TABLE 1

| Example No. | $R^1$ | $\phantom{xx}$—⟨phenyl⟩—$R^2$ | Physical constant | Amino acid |
|---|---|---|---|---|
| 2 | —CH(CH$_3$)$_2$ | —⟨C$_6$H$_4$⟩—Cl | m.p. 176° C. | i-propyloxycarbonyl-L-valine |
| 3 | —CH(CH$_3$)$_2$ | —⟨C$_6$H$_4$⟩—CH$_3$ | m.p. 160° C. | i-propyloxycarbonyl-L-valine |
| 4 | —CH(CH$_3$)$_2$ | —⟨C$_6$H$_4$⟩—Cl | m.p. 170° C. | i-propyloxycarbonyl-L-valin-(R+)-amide |
| 5 | —CH(CH$_3$)(C$_2$H$_5$) | —⟨C$_6$H$_4$⟩—Cl | m.p. 166° C. | s-butyloxycarbonyl-L-valine |
| 6 | —CH(CH$_3$)(C$_2$H$_5$) | —⟨C$_6$H$_4$⟩—CH$_3$ | m.p. 143° C. | s-butyloxycarbonyl-L-valine |
| 7 | —CH(C$_2$H$_5$)(CH$_3$) | —⟨C$_6$H$_4$⟩—OCH$_3$ | m.p. 153° C. | s-butyloxycarbonyl-L-valine |
| 8 | —CH(C$_2$H$_5$)(CH$_3$) | —⟨C$_6$H$_4$⟩—Cl | m.p. 168° C. | s-butyloxycarbonyl-L-valin-(R+)-amide |
| 9 | —CH(CH$_3$)$_2$ | —⟨C$_6$H$_4$⟩—C$_2$H$_5$ | m.p. 121–122° C. | i-propyloxycarbonyl-L-valine |
| 10 | —CH(C$_2$H$_5$)(CH$_3$) | —⟨C$_6$H$_4$⟩—C$_2$H$_5$ | m.p. 111–112° C. | s-butyloxycarbonyl-L-valine |
| 11 | —CH(CH$_3$)$_2$ | —⟨C$_6$H$_4$⟩—C$_2$H$_5$ | m.p. 154–156° C. | i-propyloxycarbonyl-L-valin-(R+)-amide |
| 12 | —CH(C$_2$H$_5$)(CH$_3$) | —⟨C$_6$H$_4$⟩—C$_2$H$_5$ | m.p. 140–142° C. | s-butyloxycarbonyl-L-valin-(R+)-amide |
| 13 | —CH(CH$_3$)$_2$ | —⟨C$_6$H$_4$⟩—CH$_3$ | m.p. 177–179° C. | i-propyloxycarbonyl-L-valin-(R+)-amide |

TABLE 1-continued

| Example No. | R¹ | aryl (R²) | Physical constant | Amino acid |
|---|---|---|---|---|
| 14 | —CH(C₂H₅)(CH₃) | —C₆H₄—CH₃ | m.p. 169–171° C. | s-butyloxycarbonyl-L-valin-(R+)-amide |
| 15 | —CH(CH₃)₂ | —C₆H₄—OCH₃ | m.p. 183–185° C. | i-propyloxycarbonyl-L-valin-(R+)-amide |
| 16 | —CH(C₂H₅)(CH₃) | —C₆H₄—OCH₃ | m.p. 178–180° C. | s-butyloxycarbonyl-L-valin-(R+)-amide |
| 17 | —CH(CH₃)₂ | —C₆H₄—Cl | 162° C. | i-Propyloxycarbonyl-D,L-valine |
| 18 | —CH(CH₃)₂ | —C₆H₄—Cl | 168° C. | i-Propyloxycarbonyl-D,L-valin-(R⁺)-Amide |
| 19 | —CH(CH₃)₂ | —C₆H₄—CH₃ | 140° C. | i-Propyloxycarbonyl-D,L-valine |
| 20 | —CH(CH₃)₂ | —C₆H₄—OCH₃ | 138° C. | i-Propyloxycarbonyl-D,L-valine |
| 21 | —CH(CH₃)₂ | —C₆H₄—CH₂CH₃ | 130° C. | i-Propyloxycarbonyl-D,L-valine |
| 22 | —CH(CH₃)₂ | —C₆H₄—CH₃ | 147° C. | i-Propyloxycarbonyl-D,L-valin-(R⁺)-Amide |
| 23 | —CH(CH₃)₂ | —C₆H₄ (m-CH₃) | 88° C. | i-Propyloxycarbonyl-D,L-valine |

USE EXAMPLES

Example A

Phytophthora Test (Tomato)/Protective

Solvent: 4.7 parts by weight of acetone
Emulsifier: 0.3 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. When the spray coating has dried on, the plants are inoculated with an aqueous spore suspension of *Phytophthora infestans*.

The plants are placed in an incubation cabin at 100% relative atmospheric humidity and approx. 20° C.

The test is evaluated 3 days after the inoculation.

In this test, an excellent fungicidal activity is shown, for example, by the compounds of Preparation Examples (1), (2), (3), (4), (5), (6), (7), (8), (9), (10), (11), (12), (13), (14), (15) and (16).

Example B

Plasmopara Test (Vines)/Protective

Solvent: 4.7 parts by weight of acetone

Emulsifier: 0.3 parts by weight of alkylaryl polyglycol ether

To prepare a suitable preparation of active compound, 1 part by Weight of active compound is mixed with the stated amounts of solvent and emulsifier, and the concentrate is diluted with water to the desired concentration.

To test for protective activity, young plants are sprayed with the preparation of active compound until dripping wet. When the spray coating has dried on, the plants are inoculated with an aqueous spore suspension of *Plasmopara viticola and then remain for* 1 day in a humid chamber at 20° to 22° C. and 100% relative atmospheric humidity. The plants are subsequently placed in a greenhouse at 22° C. and approx. 80% atmospheric humidity for 5 days. Then, the plants are moistened and placed in a humid chamber for 1 day.

The test is evaluated 7 days after the inoculation.

In this test, an excellent fungicidal activity is shown, for example, by the compounds of Preparation Examples (1), (2), (3), (4), (5), (6), (7), (8), (9), (10), (11), (12), (13), (14), (15), (16) and (23).

Example C

Plasmopara Test (Vines)/Protective

Solvent: 4.7 parts by weight of acetone

Emulsifier: 0.3 part by weight of alkylaryl polyglycl ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Plasmopara viticola* and then remain in a humidity chamber at 20° to 22° C. and 100% relative atmospheric humidity for 1 day. The plants are subsequently placed in a greenhouse at 21° C. and about 90% atmospheric humidity for 5 days. The plants are then moistened and placed in a humidity chamber for 1 day.

Evaluation is carried out 6 days after the inoculation.

In this test, a clearly superior activity compared with the prior art is shown, for example, by the compound according to the preparation Example 23, viz.:

TABLE

Plasmopara test (vines) protective

| Active compound | Degree of activity in % of the untreated control at the active compound concentration of 5 ppm |
|---|---|
| inventive: [structure (23)] | 96 |

Structure (23):
$$(CH_3)_2CH-O-CO-NH-\overset{*}{C}H(CH(CH_3)_2)-CO-NH-\overset{*}{C}H(CH_3)-C_6H_4(CH_3)$$

Example D

Alternaria Test (Tomatoes)/Protective

Solvent: 4.7 parts by weight of acetone

Emulsifier: 0.3 part weight of alkylarly polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Alternaria solani* and then remain in a humidity chamber at 20° C. and 100% relative atmospheric humidity.

Evaluation is carried out 2 days after the inoculation.

In this test, a clearly superior activity compared with the prior art is shown, for example, by the compounds according to the following preparation examples:

TABLE

Alternaria test (tomatoes)/protective

| Active compound | Degree of activity in % of the untreated control at the active compound concentration of 25 ppm |
| --- | --- |
| known: | 10 |
| inventive: 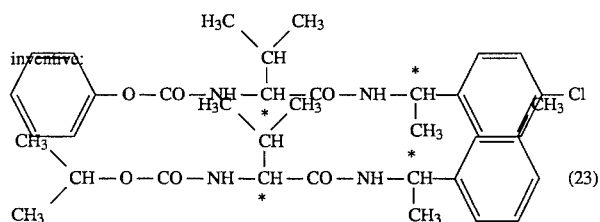 | 76 |

It will be appreciated that the instant specification and claims are set forth by way of illustration and not limitation, and that various modifications and changes may be made without departing from the spirit and scope of the present invention.

What is claimed is:

1. A valinamide derivative of the formula

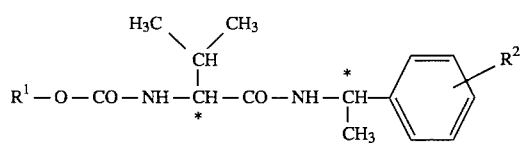

in which

R$^1$ represents i-propyl or s-butyl, and

R$^2$ represents chlorine, methyl, ethyl or methoxy in 3- or 4-position.

2. A valinamide derivative according to claim 1, formed from i-propyloxycarbonyl-L-valine or s-butoxycarbonyl-L-valine and a phenethylamine, the phenethylamine being either racemic or having the R(+) configuration or the S(−) configuration.

3. A valinamide derivative according to claim 2, in which the phenethylamine is either racemic or has the R(+) configuration.

4. A compound according to claim 1 wherein such compound is N-(i-propyl-oxycarbonyl)-L-valine-4-methoxyphenylethylamide of the formula

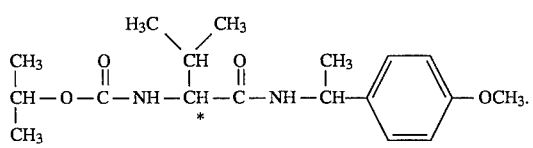

5. A compound according to claim 1 wherein such compound is N-(i-propyl-oxycarbonyl)-L-valine-4-chlorophenylethylamide of the formula

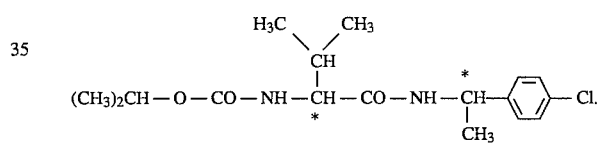

6. A compound according to claim 1 wherein such compound is N-(i-propyl-oxycarbonyl)-L-valine-4-methylphenylethylamide of the formula

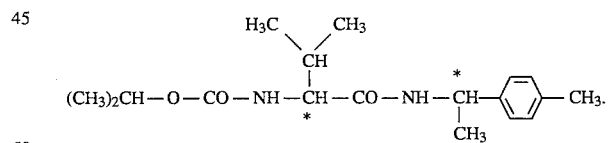

7. A compound according to claim 1 wherein such compound is N-(i-propyl-oxycarbonyl) -L-valine-4-chlorophenylethyl-(R+ )-amide of the formula

TABLE

Plasmopara test (vines) protective

| Active compound | Degree of activity in % of the untreated control at the active compound concentration of 5 ppm |
| --- | --- |
| inventive: | 96 |

TABLE-continued

Plasmopara test (vines) protective

| Active compound | Degree of activity in % of the untreated control at the active compound concentration of 5 ppm |
|---|---|

$$(CH_3)_2CH-O-CO-NH-\overset{*}{CH}(CH(CH_3)_2)-CO-NH-\overset{*}{CH}(CH_3)-C_6H_4-CH_3 \quad (23)$$

---

8. A compound according to claim 1 wherein such compound is N-(i-propyl-oxycarbonyl)-L-valine-4-ethylphenylethylamide of the formula $$(CH_3)_2CH-O-CO-NH-\overset{*}{CH}(CH(CH_3)_2)-CO-NH-\overset{*}{CH}(CH_3)-C_6H_4-C_2H_5.$$

9. A compound according to claim 1 wherein such compound is N-(i-Propyl-oxycarbonyl)-L-valine-4-ethylphenylethyl-(R+)-amide of the formula $$(CH_3)_2CH-O-CO-NH-\overset{*}{CH}(CH(CH_3)_2)-CO-NH-\overset{*}{CH}(CH_3)-C_6H_4-C_2H_5.$$

10. A compound according to claim 1 wherein such compound is N-(i-propyl-oxycarbonyl)-L-valine-4-methylphenylethyl-(R+)-amide of the formula $$(CH_3)_2CH-O-CO-NH-\overset{*}{CH}(CH(CH_3)_2)-CO-NH-\overset{*}{CH}(CH_3)-C_6H_4-CH_3.$$

11. A compound according to claim 1 wherein such compound is N-(i-propyl-oxycarbonyl)-L-valine-4-methoxyphenylethyl-(R+)-amide of the formula $$(CH_3)_2CH-O-CO-NH-\overset{*}{CH}(CH(CH_3)_2)-CO-NH-\overset{*}{CH}(CH_3)-C_6H_4-OCH_3.$$

12. A compound according to claim 1 wherein such compound is N-(i-propyl-oxycarbonyl)-D,L-valine-4-chlorophenylethylamide of the formula $$(CH_3)_2CH-O-CO-NH-\overset{*}{CH}(CH(CH_3)_2)-CO-NH-\overset{*}{CH}(CH_3)-C_6H_4-Cl.$$

13. A compound according to claim 1 wherein such compound is N-(i-propyl-oxycarbonyl)-D,L-valine-4-chlorophenylethyl-(R+)-amide of the formula $$(CH_3)_2CH-O-CO-NH-\overset{*}{CH}(CH(CH_3)_2)-CO-NH-\overset{*}{CH}(CH_3)-C_6H_4-Cl.$$

14. A compound according to claim 1 wherein such compound is N-(i-propyl-oxycarbonyl)-D,L-valine-4-methylphenylethylamide of the formula $$(CH_3)_2CH-O-CO-NH-\overset{*}{CH}(CH(CH_3)_2)-CO-NH-\overset{*}{CH}(CH_3)-C_6H_4-CH_3.$$

15. A compound according to claim 1 wherein such compound is N-(i-propyl-oxycarbonyl)-D,L-valine-4-methoxyphenylethylamide of the formula $$(CH_3)_2CH-O-CO-NH-\overset{*}{CH}(CH(CH_3)_2)-CO-NH-\overset{*}{CH}(CH_3)-C_6H_4-OCH_3.$$

16. A compound according to claim 1 wherein such compound is N-(i-propyl-oxycarbonyl)-D,L-valine-4-ethylphenylethylamide of the formula

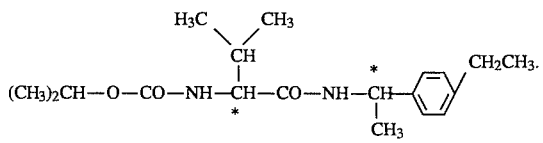

17. A compound according to claim 1 wherein such compound is N-(i-propyl-oxycarbonyl)-D,L-valine-4-methylphenylethyl-(R+ )-amide of the formula

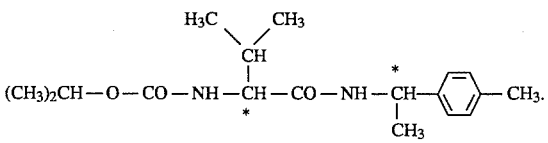

18. A compound according to claim 1 wherein such compound is N-(s-butyloxycarbonyl)-L-valine-4-chlorophenylethylamide of the formula

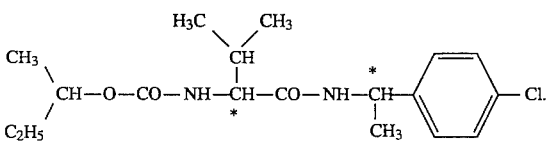

19. A compound according to claim 1 wherein such compound is N-(s-butyloxycarbonyl)-L-valine-4-methylphenylethylamide of the formula

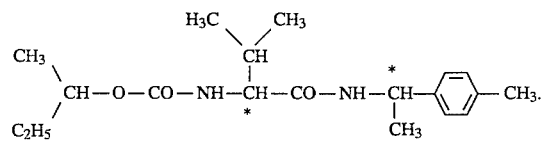

20. A compound according to claim 1 wherein such compound is N-(s-butyloxycarbonyl)-L-valine-4-methoxyphenylethylamide of the formula

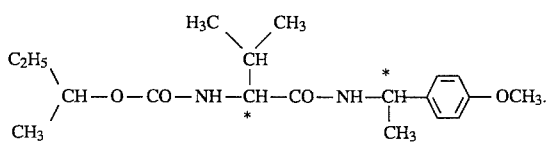

21. A compound according to claim 1 wherein such compound is N-(s-butyloxycarbonyl)-L-valine-4-chlorophenylethyl-(R+ )-amide of the formula

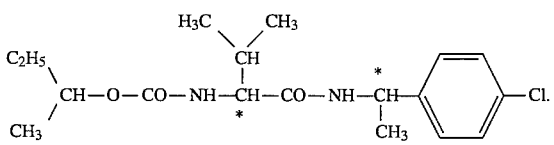

22. A compound according to claim 1 wherein such compound is N-(s-butyloxycarbonyl)-L-valine-4-ethylphenylethylamide of the formula

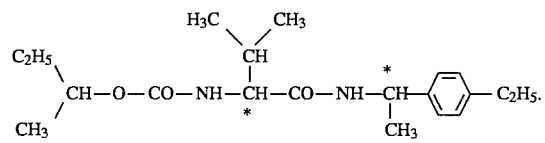

23. A compound according to claim 1 wherein such compound is N-(s-butyloxycarbonyl)-L-valine-4-ethylphenylethyl-(R+ )-amide of the formula

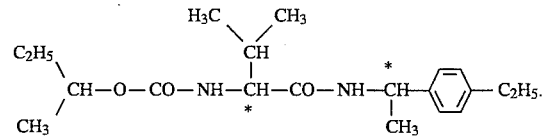

24. A compound according to claim 1 wherein such compound is N-(s-butyloxycarbonyl)-L-valine-4-methylphenylethyl-(R+ )-amide of the formula

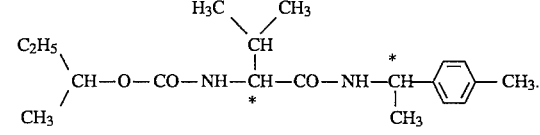

25. A compound according to claim 1 wherein such compound is N-(s-butyl-oxycarbonyl)-L-valine-4-methoxyphenylethyl-(R+ )-amide of the formula

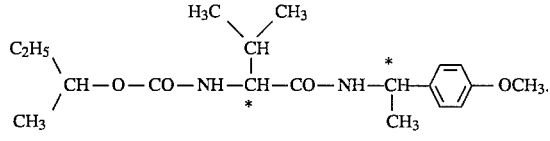

26. A compound according to claim 1 wherein such compound is N-(i-propyl-oxycarbonyl)-L-valine-3-methylphenylethylamide of the formula

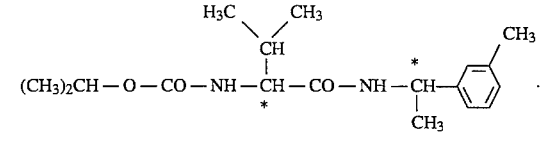

27. A fungicidal or insecticidal composition comprising a fungicidally or insecticidally effective amount of at least one valinamide derivative according to claim 1 and a carrier.

28. A method of combating fungi or insects which comprises applying to such fungi, insects or a habitat thereof a fungicidally or insecticidally effective amount of a valinamide derivative according to claim 1.

29. The method according to claim 28, wherein such compound is
N-(i-propyl-oxycarbonyl)-L-valine-4-methoxyphenylethylamide,
N-(i-propyl-oxycarbonyl)-L-valine-4-chlorophenylethylamide,
N-(i-propyl-oxycarbonyl)-L-valine-4-methylphenylethylamide, N-(i-propyl-oxycarbonyl)-L-valine-4-chlorophenylethyl-(R+)-amide,
N-(S-butyloxycarbonyl)-L-valine-4-chlorophenylethylamide,
N-(S-butyloxycarbonyl)-L-valine-4-methylphenylethylamide,
N-(S-butyloxycarbonyl)-L-valine-4-methoxyphenylethylamide,
N-(S-butyloxycarbonyl)-L-valine-4-chlorophenylethyl-(R+)-amide,
N-(i-propyl-oxycarbonyl)-L-valine-4-ethylphenylethylamide,
N-(S-butyloxycarbonyl)-L-valine-4-ethylphenylethylamide,
N-(i-propyl-oxycarbonyl)-L-valine-4-ethylphenylethyl-(R+)-amide,
N-(S-butyloxycarbonyl)-L-valine-4-ethylphenylethyl-(R+)-amide,
N-(i-propyl-oxycarbonyl)-L-valine-4-methylphenylethyl-(R+)-amide,
N-(S-butyloxycarbonyl)-L-valine-4-methylphenylethyl-(R+)-amide,
N-(i-propyl-oxycarbonyl)-L-valine-4-methoxyphenylethyl-(R+)-amide,
N-(S-butyl-oxycarbonyl)-L-valine-4-methoxyphenylethyl-(R+)-amide,
N-(i-propyl-oxycarbonyl)-D,L-valine-4-chlorophenylethylamide,
N-(i-propyl-oxycarbonyl)-D,L-valine-4-chlorophenylethyl-(R+)-amide,
N-(i-propyl-oxycarbonyl)-D,L-valine-4-methylphenylethylamide,
N-(i-propyl-oxycarbonyl)-D,L-valine-4-methoxyphenylethylamide,
N-(i-propyl-oxycarbonyl)-D,L-valine-4-ethylphenylethylamide,
N-(i-propyl-oxycarbonyl)-L-valine-3-methylphenylethylamide or
N-(i-propyl-oxycarbonyl)-D,L-valine-4-methylphenylethyl-(R+)-amide.

* * * * *